United States Patent [19]  [11] 4,402,228
Eberle  [45] Sep. 6, 1983

[54] APPARATUS AND METHOD FOR TESTING THE HARDNESS OF BATTERY COMPONENTS

[75] Inventor: William J. Eberle, Reading, Pa.

[73] Assignee: General Battery Corporation, Reading, Pa.

[21] Appl. No.: 270,495

[22] Filed: Jun. 4, 1981

[51] Int. Cl.³ ............................................. G01N 3/20
[52] U.S. Cl. ......................................... 73/849; 73/81; 73/87; 73/432 R
[58] Field of Search ..................... 73/81, 87, 849, 850, 73/862.38, 432 Z, 4 R; 200/153 T; D10/64; 408/115 R, 115 B

[56] References Cited

U.S. PATENT DOCUMENTS 2,564,582  8/1951  Rockwell .............................. 60/534
2,604,702  7/1952  Collins .................................. 33/174 B
2,875,608  3/1959  Englehardt et al. .................. 73/187
3,775,020  11/1973  Stoutenberg ...................... 33/189 X
3,934,463  2/1976  Venderjagt ............................. 73/81
4,166,210  8/1979  Eberle ................................. 219/119
4,247,744  2/1981  Birkle .......................... 200/153 T X

FOREIGN PATENT DOCUMENTS 702372  1/1965  Canada .......................... 200/153 T
808832  2/1959  United Kingdom ................ 408/115
1096169  12/1967  United Kingdom .................... 73/81

OTHER PUBLICATIONS

"The Rockwell Tester", Acco Industries, Inc., Wilson Instrument Div., Bridgeport, Conn., 1980.

Primary Examiner—E. R. Kazenske
Assistant Examiner—Tom Noland
Attorney, Agent, or Firm—Benasutti and Murray

[57] ABSTRACT

An apparatus and method for determining the hardness characteristics of battery components such as lead intercell connection lugs wherein a base is provided with an aperture which corresponds to the size of the aperture provided in the intercell partition of a battery container, and a retractable ram is positioned in substantial axial alignment with the aperture in the base, so that the battery component can be positioned on the base and over the aperture and so that the retractable ram can be advanced into contact with the battery component so that the battery component is extruded into the aperture. When the battery component is extruded into the aperture for a selected distance, a limit switch is activated, whereupon the force applied to the ram is measured.

21 Claims, 7 Drawing Figures

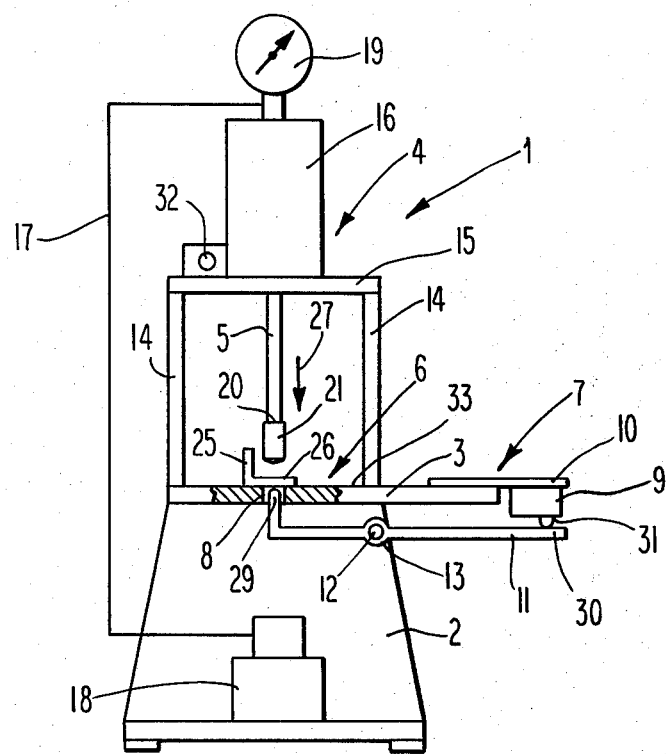
Fig. 1
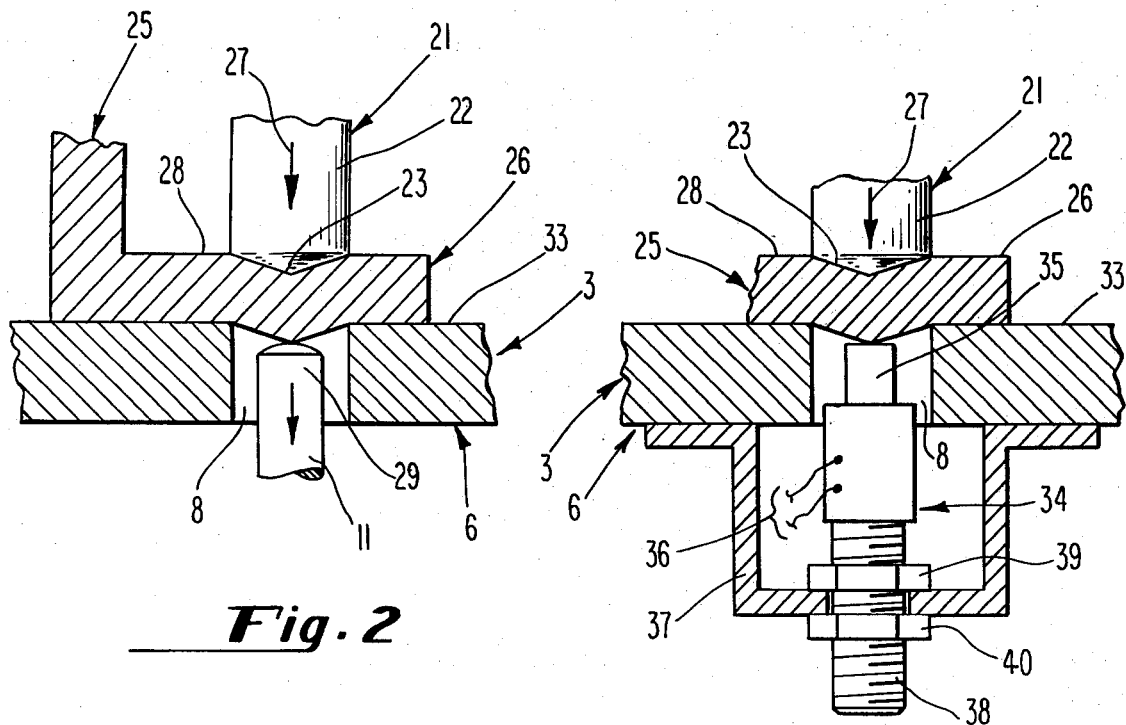
Fig. 2
Fig. 3

APPARATUS AND METHOD FOR TESTING THE HARDNESS OF BATTERY COMPONENTS

BACKGROUND OF THE INVENTION

The present invention relates generally to the field of hardness testing, and in particular, to an apparatus and method for testing the hardness of battery components such as battery lugs.

A typical automotive battery generally includes a container which is separated into a plurality of compartments by a series of partitions, and a plurality of cell groups which are positioned within each of the compartments and appropriately interconnected to complete the assembled battery. Each cell group typically comprises a series of interleaved positive and negative plates; respective positive and negative plates being appropriately interconnected by straps extending therebetween. To assemble the finished battery, these straps must be appropriately interconnected so that the positive strap of one cell group is connected to the negative strap of an adjacent cell group. One way that this may be accomplished is by providing each of the partitions with an aperture, and by providing each of the battery straps with an upstanding lug positioned so that adjacent lug pairs can be connected to each other through the aperture of the partition using any of a variety of techniques. One technique which can be used for the purpose is resistance welding. Examples of this may be found, for example, in my U.S. Pat. No. 4,166,210, the subject matter of which is hereby incorporated by reference as if fully set forth herein.

Generally, the technique illustrated in U.S. Pat. No. 4,166,210 calls for flat outer surfaces of the battery lugs to be positioned adjacent the partition and substantially enclosing the aperture. Thereafter, a pair of weld jaws are positioned adjacent the exposed surfaces of the battery lugs so that electrodes attached to the weld jaws can extrude portions of the lug material into the aperture of the partition. Upon achieving proper contact, an electric current is directed through the weld jaws, the electrodes and the battery lugs. A strong and efficiently produced weld results, providing the desired intercell connection.

The foregoing technique has been found to work extremely well in providing strong and efficiently produced intercell welds. However, despite the improvements afforded by such a technique, it has been found that a significant number of batteries still must be rejected for failure to achieve a proper intercell weld. Since a typical automotive battery generally includes five such welds, the problem is multiplied, since the failure of any one of these welds can result in rejection of the battery. For this reason, continued attempts have been made to further refine this technique.

One variable which has been found to affect weld performance relates to the amount of pressure which must be applied to the battery lugs to achieve their proper contact whithin the aperture of the partition. Applying too much pressure can cause excessive contact between the battery lugs, while applying too little pressure can cause insufficient contact. In either case, an improper resistance is developed across the battery lugs, adversely affecting the resulting weld. However, by properly regulating the pressure applied to the battery lugs, substantially improved intercell welds can be produced.

One difficulty which has been encountered in satisfactorily regulating the pressures applied by the weld jaws relates to the non-uniformity in hardness of such battery lugs, particularly between different production lots. Clearly, variations in hardness can adversely affect the amount of lug contact produced when a given pressure is applied by the weld jaws. It is therefore desirable to obtain an accurate indication of the hardness of the battery lugs being used in a particular application before the operational parameters of the welding apparatus are set.

A variety of devices have been used in an attempt to obtain such a measurement. Perhaps the most sophisticated hardness tester used for this purpose is the Rockwell Model JS Hardness Tester, however, satisfactory results have still not generally been obtained. Rather, substantial variations have often been found to occur between measurements performed on lugs from different, or even the same production lots, and even between separate measurements performed at two different locations on a single lug. Moreover, a surprising lack of corrolation has been found to exist between the hardness value measured by the hardness tester and the actual performance of the intercell welding apparatus after being set to accommodate a battery lug having such a hardness value. Such variations have made it exceedingly difficult to accurately predict the amount of pressure which must be applied by the weld jaws to achieve a proper intercell weld.

It, therefore, remains desirable to develop an apparatus which can accurately and reliably determine the hardness of a battery lug, so that the intercell welding apparatus can be calibrated to achieve a proper intercell weld.

SUMMARY OF THE INVENTION

In accordance with the present invention, an apparatus is provided for testing the hardness of battery components, such as the battery lugs, which generally comprises a table, having an aperture extending therethrough and including a limit switch operatively associated therewith, and a retractable ram positioned in substantial alignment with the aperture of the table and adapted to advance toward and away from the aperture in substantial alignment therewith.

In use, a battery lug is positioned on the table of the apparatus so that portions of the lug cover the aperture. The ram is then advanced toward the aperture and into contact with the battery lug. A sufficient pressure is applied to the ram to force the material forming the battery lug into the aperture, and into contact with the limit switch. By positioning the limit switch at a location which substantially corresponds to one half the thickness of a typical battery partition, the amount of force which must be applied to the battery lug to properly advance the battery lug material into such an aperture is simulated. The amount of force applied to the ram is then measured, and this value is used to properly calibrate the jaws of the intercell welder, contributing to a substantially improved intercell weld.

Accordingly, it is a primary object of the present invention to develop a method which can be used to accurately determine the hardness characteristics of a battery component, particularly the lugs used to provide intercell connections within an assembled battery.

It is also an object of the present invention to develop a method which can be used to determine the hardness characteristics of a battery lug by simulating the actual conditions encountered when such battery lugs are welded together to form an intercell connection.

It is also an object of the present invention to develop an apparatus which can be used to accurately determine the hardness characteristics of a battery component, by simulating the actual conditions encountered when such a battery component is used in assembling the battery.

These and other objects will become apparent from the following detailed description, taken in conjunction with the following illustrations.

BRIEF DESCRIPTION OF THE DRAWINGS

FIG. 1 is a partial, side elevational view of an apparatus produced in accordance with the present invention to measure the hardness characteristics of a battery lug.

FIG. 2 is a fragmentary, cross-sectional view illustrating the manner in which the ram advances the battery lug material into the aperture and into contact with the limiting switch.

FIG. 3 is a fragmentary, cross-sectional view similar to that of FIG. 2, also showing an alternative embodiment limiting switch located within the aperture.

In the several views provided, like reference numerals denote similar structure.

DETAILED DESCRIPTION OF THE PREFERRED EMBODIMENT

Figure 4:
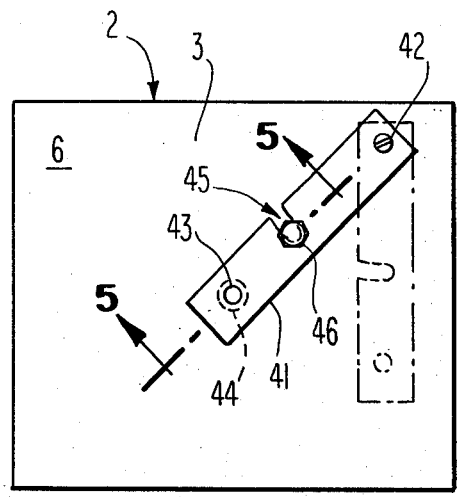
FIG. 4 is a top plan view of the table of the apparatus of FIG. 1, also showing an alternative means for varying the location of the limiting switch within the aperture.

Although specific forms of the invention have been selected for illustration in the drawings, and the following description is drawn in specific terms for the purpose of describing these forms of the invention, this description is not intended to limit the scope of the invention which is defined in the appending claims.

Referring now to FIG. 1, a preferred embodiment test apparatus 1 is illustrated. The apparatus 1 generally comprises a base 2, the upper portions of which are provided with a surface or table 3, and a head frame assembly 4 positioned over the table 3 and adapted to support a retractable ram 5 in position as shown. The configuration of the major structural features comprising the apparatus 1 may be varied according to need and convenience, however, the configuration illustrated in the drawings is preferred.

The table 3 includes a first, centrally disposed section 6 which forms the top of the base 2, and a second, extension section 7 extending laterally outwardly from the base 2. The central section 6 of the base 2 is provided with an aperture 8 having a configuration which preferably corresponds to that of the aperture in the partition wall of the type of battery being assembled, as will be more fully described below. The extension section 7 of the base 2 is provided with a limiting switch 9. The limiting switch 9 may be attached to the extension section 7 using any of a variety of techniques, one example being the bracket 10 illustrated. A lever arm 11 extends between the limiting switch 9 and the aperture 8 and is capable of movement about a pivot 12 associated with the base 2 of the apparatus 1. The pivot 12 engages a bearing 13 associated with the lever arm 11 permitting free rotation of the lever arm 11, and accordingly, operation of the limiting switch 9.

The head frame assembly 4 generally comprises a head frame 15 which is supported in position over the central section 6 of the base 2 using, for example, the support brackets 14 illustrated. A piston 16 is connected to the head frame 15 so that the ram 5, which is associated with the piston 16, extends downwardly from the head frame 15 toward the base 2 of the apparatus 1. The several components comprising the head frame assembly 4 are oriented so that the ram 5 operatively associated with the piston 16 is substantially axially aligned with the aperture 8 provided in the central section 6 of the base 2. To provide the apparatus 1 with maximum structural integrity, it is preferred that the ram 5 and the aperture 8 are both located substantially centrally within the apparatus 1.

In the preferred embodiment, the piston 16 is pneumatically operated. Operation of the piston 16 is therefore accomplished via supply line 17, which communicates between the piston 16 and an intensifier 18, which can be operated from any conventional source. In order to provide a measurement of the characteristics of the component being tested, a meter 19 is also provided. A variety of conventional meters may be used for this purpose, and may be associated with the apparatus at a variety of different locations including the intensifier 18, the supply line 17 or the piston 16. Of course, other types of devices may also be used to operate the ram 5 with similar results, if desired.

The lower end 20 of the ram 5 is preferably provided with an electrode 21 having surface characteristics similar to the electrodes which are used to actually perform the intercell connection. This is preferred so that the apparatus 1 can be fitted with electrodes having different sizes and shapes, to accommodate a wide variety of test conditions. However, it is also possible for the lower end 20 of the ram 5 to be shaped in the form of an electrode, eliminating the need to use a separate electrode 21, if indicated for a particular application. The electrode 21 illustrated generally comprises a cylindrical body 22 having a conical projection 23, however, electrodes having other surface characteristics may also be used. The electrode 21 is preferably attached to the ram 5 using the same means by which the electrode would be attached to the jaws of an intercell welder, for example, by threadingly engaging the lower end 20 of the ram 5. In this manner, the same electrodes which are used to perform the intercell weld can be used in the apparatus 1.

Having described the structure comprising the apparatus 1, its method of use will now be discussed. A lug 25 of the type which is to be used to form intercell connections is positioned on the base 2 of the apparatus 1 so that the upstanding portion 26 of the lug 25 (the portion which would normally be positioned adjacent the battery partition) lies on the base 2 with portions of the lug material covering the aperture 8. As previously discussed, the diameter of the aperture 8 is selected to substantially correspond to the diameter of the apertures which will be provided in the partitions of the battery cases to be assembled. As a result, this alignment creates an environment which is substantially equivalent to that which will be encountered by the weld jaws when the actual intercell weld is being performed. Accordingly, downward advancement of the ram 5, as indicated by the arrow 27, will cause the electrode 21 to contact the exposed surface 28 of the upstanding portion 26 of the lug 25. Applying further pressure to the ram 5 will cause the material forming the lug 25 to be extruded downwardly and into the aperture 8, as illustrated in FIG. 2, and toward the terminating portion 29 of the lever arm 11. This application of pressure may be advantageously regulated using the intensifier 18. As the terminating portion 29 of the lever arm 11 is contacted by the material forming the lug 25, the terminating portion 29 is advanced downwardly, which causes the lever arm 11 to rotate about the pivot 12 so that the end 30 of the lever arm 11 depresses the contact 31 of the limiting switch 9. This contacting of the limiting switch 9 can be used to operate a variety of indicators, such as a panel light or buzzer 32, providing an active means for determining when the terminating portion 29 of the lever arm 11 has been contacted by the material forming the lug 25. By adjusting the positioning of the terminating portion 29 of the lever arm 11 with respect to the outer surface 33 of the base 2, the manner in which a battery lug is extruded into the partition of a battery container is accurately simulated.

The foregoing simulates an extrusion-fusion weld. Accordingly, by reading the amount of force required to advance the ram downwardly into the battery lug 25, using the meter 19, an accurate measurement of the hardness characteristics of the lug 25 is obtained. This measurement may then be used to determine the pressure which should be applied by the jaws of the welding apparatus to perform a satisfactory intercell weld.

It may therefore be seen that the foregoing apparatus serves well to satisfy each of the several objectives previously set forth. However, it is also to be understood that the foregoing apparatus may be modified without departing from the scope of the present invention. For example, the configuration of the apparatus 1 may be varied as long as the proper structural interrelationships are provided between the ram 5, the lug 25, the aperture 8 of the base 2, and the means used to operate the limiting switch 9. Moreover, a variety of different devices may be used to advance the ram 5 as previously described. In fact, the ram 5 need not reciprocate in a vertical direction as shown, but may also reciprocate in other directions, if desired.

In addition, the limiting switch selected for use in conjunction with the apparatus 1 may also be varied. For example, the limiting switch 9 illustrated in FIG. 1 utilizes a lever arm 11 which extends between the aperture 8 and a remotely positioned limiting switch 9. As illustrated in FIG. 3, it is also possible to provide a limiting switch 34 which is positioned directly within the aperture 8 of the apparatus 1, thereby eliminating the need for the lever arm 11. As shown, a conventional contact switch may be used for this purpose, the button 35 of the switch 34 being used to detect movement of the material forming the lug 25 into the aperture 8. Depression of the button 35 operates the panel light or buzzer previously described via the connection leads 36. As shown in FIG. 3, the limiting switch 34 may be advantageously mounted within the aperture 8 utilizing a U-shaped bracket 37 attached to and beneath the base 2 of the apparatus 1, using appropriate hardware.

As a further variation, it may often be desirable to provide the apparatus 1 with an adjustment feature which is capable of correlating operation of the apparatus 1 to any of a variety of different partition and aperture sizes. To do so, it is desirable that the diameter of the aperture 8 as well as the depth to which the material forming the battery lug 25 must proceed in order to operate the limiting switch be variable. Such adjustment may be performed in a variety of ways.

Figure 5:
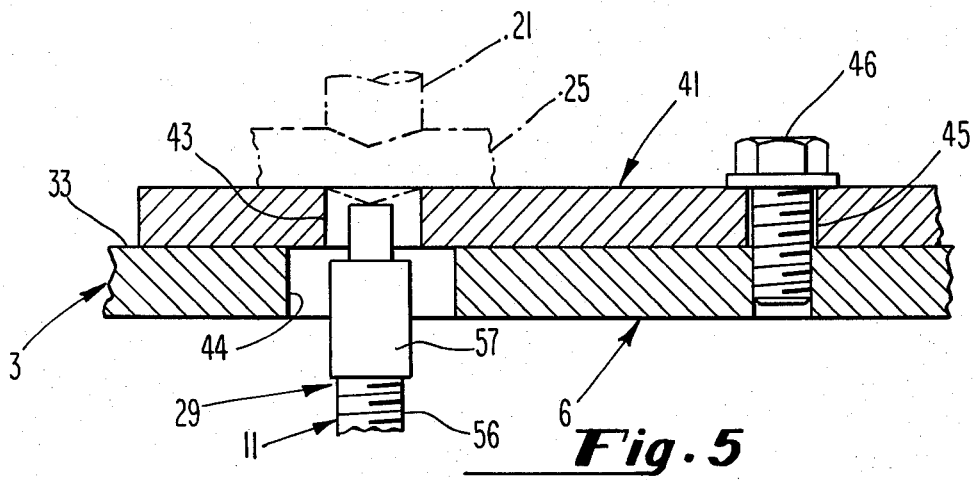
FIG. 5 is a fragmentary, cross-sectional view illustrating the alternative means of FIG. 4, taken along line 5—5.
Figure 7:
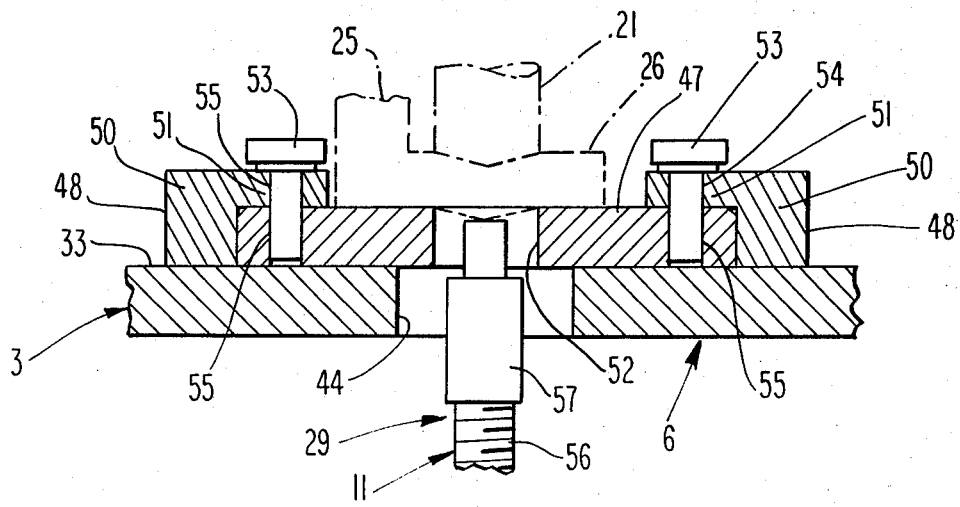
FIG. 7 is a fragmentary, cross-sectional view illustrating the alternative means of FIG. 6, taken along line 7—7.

For example, referring to the embodiment illustrated in FIG. 1, the location of the terminating portion 29 of the lever arm 11 within the aperture 8 may be regulated by varying the extension of the contact 31 from the limiting switch 9, for example, by using a limiting switch 9 which has a contact 31 which is threadingly associated with the remainder of the body of the limiting switch so that rotation of the contact 31 advances it toward or away from the end 30 of the lever arm 11. Alternatively, shims may be used in conjunction with the bracket 10 which connects the base 2 and the limiting switch 9. The length of the terminating portions 29, 30 of the lever arm 11 may also be varied to provide this function. For example, as illustrated in FIGS. 5 and 7, the terminating end 29 of the lever arm 11 may be provided with an external, threaded portion 56 adapted for engagement by the inner threaded portion of a cap 57. Rotation of the cap 57 varies the extension of the terminating end 29 of the lever arm 11 into the aperture 8. Other adjustment mechanisms may also be used. However, irrespective of the device used, the location of the terminating end 29 of the lever arm 11 within the aperture 8 will vary, enabling the simulation of partitions having different thicknesses.

Referring to the embodiment illustrated in FIG. 3, such adjustment may be provided by using a limiting switch 34 which is capable of threadingly engaging the bracket 37. By adjusting the relative positioning between the threaded portion 38 of the switch 34 and the bracket 37, the distance between the button 35 and the outer surface 33 of the base 2 is varied. Upon achieving proper spacing, the backing nut 40 may be tightened against the bracket 37, thereby maintaining the limiting switch 34 in its desired position.

The foregoing discusses ways in which adjustment of the positioning of the limiting switch 9 may be used to simulate variations in partition thickness. In many applications it may also be desirable to vary the diameter of the simulated aperture, in addition to simulating different partition thicknesses. Moreover, it may often be desirable to provide these adjustements without having to operate threaded structures, avoiding the need for precise operations.

One such apparatus which can be used for this purpose is illustrated in FIGS. 4 and 5. As shown, the table 2 has been provided with a template 41 which is pivoted for rotation with respect to the base 2 about a pivoting screw 42. The end of the template 41 opposite to the pivoting screw 42 is provided with an aperture 43. The diameter and depth of the aperture 43 are selected to combine with the aperture 44 in the base 2 to simulate the aperture of a battery partition. For this reason, it is generally preferred that the aperture 44 of the base 2 have a diameter which equals or exceeds the diameter of the largest aperture size to be tested to assure that the aperture 44 is never smaller in diameter than the aperture 43 of the template 41 which is being used. The template 41 is also provided with a slotted recess 45 which is positioned to engage a bolt 46 associated with the base 2 of the apparatus 1. By properly correlating the recess 45 with the location of the bolt 46, proper positioning of the template 41 is provided by simply rotating the template 41 into position as shown, and by tightening the bolt 46 to maintain the template 41 in its proper position. Clearly, although only one template 41 is illustrated in FIGS. 4 and 5, it is to be understood that additional templates may also be provided which have different aperture diameters and different thicknesses. In this manner, the apparatus 1 can be used to test battery lugs under a variety of different operating conditions. Moreover, these templates can be quickly changed, without requiring any special alignment procedure, when a different test procedure is to be performed.

Figure 6:
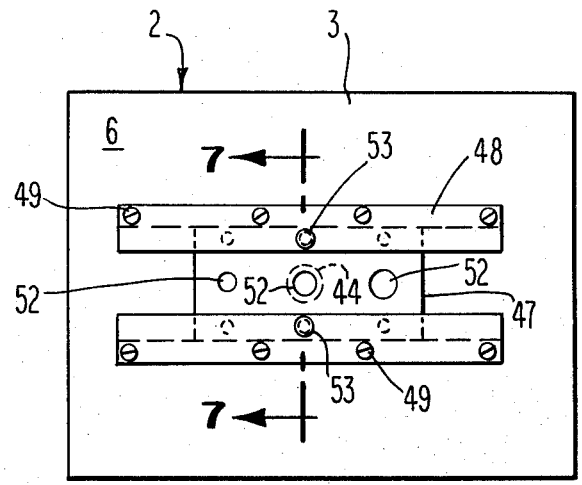
FIG. 6 is a top plan view of the table of the apparatus of FIG. 1, also showing an alternative means for varying the location of the limiting switch within the aperture.

FIGS. 6 and 7 illustrate an alternative embodiment template 47 which can also be used in conjunction with the apparatus 1 of the present invention to test battery lugs under a variety of different conditions. As shown, the base 2 of the apparatus 1 is provided with a pair of opposed, spaced rails 48 which are attached to the base 2 using a plurality of screws, or other similar fasteners. As illustrated in FIG. 7, the rails 48 comprise a body 50, and a track 51 extending transversly outwardly from the upper end of the body 50. This defines a space capable of slidingly engaging a template 47. By providing the template 47 with a series of sized apertures 52 having different diameters and thicknesses, battery lugs may be tested under a variety of conditions. All that need be done to select the aperture 52 which is to be used to perform the test is to slide the template 47 into position so that the selected aperture is in alignment with the aperture 44 of the apparatus. A variety of mechanisms may then be used to properly maintain the template 47 in its desired position. For example, as illustrated in FIGS. 6 and 7, a pair of pins 53 may be used which extend between apertures 54 in the tracks 51 of the rails 48 and apertures 55 provide in the template 47. Other mechanisms may also be used for this purpose, such as spring loaded ball detents or the like.

It will also be understood that various changes in the details, materials and arrangements of parts which have been herein described and illustrated in order to explain the nature of this invention may be made by those skilled in the art within the principal and scope of the invention as expressed in the following claims.

What is claimed is:

1. An apparatus for determining the deformability of a component, which apparatus comprises:
   a. a base having an aperture disposed therein;
   b. a ram operatively associated with the base and located in substantial axial alignment with the aperture;
   c. limiting switch means comprising lever means, one portion of which extends into the aperture and the other portion of which is operatively associated with a switch, so that contact between the component and the portion of the lever means located within the aperture causes operation of the switch; and
   d. means for advancing the ram with respect to the aperture;
   whereby a component positioned on the base and over the aperture is capable of being advanced by the ram, into the aperture, and into contact with the limiting switch means.

2. The apparatus of claim 1 wherein the component is an upstanding lug used to form a battery intercell connection.

3. The apparatus of claim 2 wherein the aperture is sized to correspond to the size of an aperture in a partition of a battery container.

4. The apparatus of claim 2 wherein the configuration of the terminating end of the ram corresponds to the configuration of an electrode used to perform an intercell weld.

5. The apparatus of claim 1 wherein the terminating end of the ram is conical.

6. The apparatus of claim 1 wherein the advancing means is a pneumatically operated piston.

7. The apparatus of claim 6 wherein the advancing means further comprises intensifier means for varying the force applied to the piston.

8. The apparatus of claim 1 further comprising means for measuring an amount of force required to cause the ram to advance the component into contact with the limiting switch means.

9. The apparatus of claim 1 wherein the positioning of the lever means within the aperture is adjustable.

10. The apparatus of claim 1 further comprising indicator means operatively associated with the switch and adapted to indicate contact between the component and the limiting switch means.

11. The apparatus of claim 1 further comprising template means for varying the configuration of the aperture.

12. The apparatus of claim 11 wherein the template means comprises:
   a. a template having an aperture at one end and pivotable about the other end; and
   b. means for fixing the template in position so that the aperture of the template aligns with the aperture of the base.

13. The apparatus of claim 12 wherein the diameter of the aperture of the template is no greater than the diameter of the aperture of the base.

14. The apparatus of claim 11 wherein the template means comprises:
   a. a pair of opposing spaced rails; and
   b. a template slidingly engaged by the rails and having a plurality of apertures therein.

15. The apparatus of claim 14 further comprising means for maintaining the template in a selected position.

16. The apparatus of claim 14 wherein the plurality of apertures have different diameters, and wherein the diameter of the largest aperture is no greater than the diameter of the aperture of the base.

17. An apparatus for determining the deformability of a component, which apparatus comprises:
   a. a base having an aperture disposed therein;
   b. a ram operatively associated with the base and located in substantial axial alignment with the aperture;
   c. limiting switch means comprising a bracket located adjacent the aperture and attached to the base of the apparatus, and a switch attached to the bracket and extending into the aperture; and
   d. means for advancing the ram with respect to the aperture;
   whereby a component positioned on the base and over the aperture is capable of being advanced by the ram, into the aperture, and into contact with the limiting switch means.

18. The apparatus of claim 17 wherein the positioning of the switch within the aperture is adjustable.

19. A method for determining the deformability of a component, which method comprises:
   a. providing a test apparatus having a base including an aperture;
   b. positioning the component on the base and over the aperture;
   c. advancing a ram assoicated with the test apparatus toward the component and the aperture of the base;
   d. urging material forming the component into the aperture by advancement of the ram;
   e. sensing when the material has been urged into the aperture for an adjustable, selected distance; and
   f. determining the amount of force applied to the ram to urge the material into the aperture for the selected distance.

20. The method of claim 19 wherein the ram is substantially axially aligned with the aperture.

21. The method of claim 14 wherein the component completely covers the aperture of the base.

* * * * *